United States Patent

Harrison

[11] 3,937,085
[45] Feb. 10, 1976

[54] THERMOMETER
[75] Inventor: Burton H. Harrison, Weston, Mass.
[73] Assignee: Selective Educational Equipment, Inc., Newton, Mass.
[22] Filed: Feb. 3, 1972
[21] Appl. No.: 223,103

[52] U.S. Cl. .................... 73/338.6; 73/376; 73/338
[51] Int. Cl.² .......................................... G01K 1/14
[58] Field of Search ............ 73/376, 374, 377, 378, 73/338, 338.6; 206/DIG. 6

[56] References Cited
UNITED STATES PATENTS

| | | | |
|---|---|---|---|
| 332,947 | 12/1885 | Sardy et al. ............................. | 73/376 |
| 1,842,072 | 1/1932 | Collingbourne ............... | 206/DIG. 6 |
| 1,977,711 | 10/1934 | Bandoly ................................ | 73/376 |
| 2,021,070 | 11/1935 | Levine ......................... | 206/DIG. 6 |
| 2,119,126 | 5/1938 | Bising .................................... | 73/376 |
| 2,201,186 | 5/1940 | Lane .................................... | 73/376 |
| 2,272,240 | 2/1942 | Edwards ............................... | 73/374 |
| 2,608,863 | 9/1952 | Erbguth ................................ | 73/376 |
| 2,841,010 | 7/1958 | Garret................................... | 73/376 |
| 2,894,391 | 7/1959 | Colt................................... | 73/338.6 |

OTHER PUBLICATIONS

Webster New World Dictionary of the American Language, copyright 1957; page 1272.

*Primary Examiner*—S. Clement Swisher
*Assistant Examiner*—Denis E. Corr
*Attorney, Agent, or Firm*—Wolf, Greenfield & Sacks

[57] ABSTRACT

A thermometer and a generally elongate mount therefor in which the mount is of channel-shaped cross-section defined by sidewalls which converge along an apex. The thermometer is retained within the channel along the apex by bands which pass through the mount and are looped about the thermometer so that the sidewalls flank and embrace the thermometer. The inner surface of each of the sidewalls is calibrated with centigrade and fahrenheit temperature scales. Various openings are formed in the mount to enable it to be hung, as from a string, and also to enable it to be employed as a sling psychrometer.

12 Claims, 5 Drawing Figures

THERMOMETER

BACKGROUND OF THE INVENTION

This invention relates to an improved thermometer and mounting device which renders the thermometer highly versatile. The thermometer is suited particularly for use in a demonstrative or educational environment such as in a classroom or laboratory.

SUMMARY OF THE INVENTION

The invention includes an elongate mount or backing element which defines an elongate channel or trough. The thermometer tube is retained along and within the bottom of the trough by bands which are looped about the upper and lower ends of the thermometer tube and which extend rearwardly through holes formed in the backing member. The portions of the bands which extend rearwardly through the channel are secured to the channel to retain the ends of the thermometer tube firmly in place. The sidewalls of the backing which define the channel and which embrace the thermometer tube are calibrated with temperature scales extending along their length on each side of the thermometer tube. Appropriate holes are formed in the backing member to enable the bands to pass therethrough. Additionally, an appropriate hole is formed at the upper end of the backing member to enable the device to be suspended from the string or to be employed as a sling psychrometer.

The thermometer tube is recessed well within the channel and thus is protected from inadvertent breakage. Additionally, because the thermometer is recessed well within the channel, the bulb of the thermometer tube may be covered with moist tissue which is retained within the channel by an elastic band. This enables the device to be employed as a sling psychrometer.

In one embodiment of the invention, the thermometer tube is retained in the channel by elastic bands which may be removed easily to release the thermometer tube from the channel. This is desirable in those instances where the thermometer is to be inserted through a relatively small opening which cannot receive the cross-sectional dimensions of the mounting member itself.

Among the primary objects of the invention is to provide an improved thermometer and calibrated support bracket therefor which is suited for use particularly in an educational environment such as in classroom or laboratory.

A further object of the invention is to provide an improved thermometer and backing which is of simplified, inexpensive construction.

A further object of the invention is to provide an improved thermometer and backing therefor in which the thermometer is protected by the backing.

Another object of the invention is to provide a thermometer and backing therefor which permit use either as a thermometer or as a sling psychrometer.

Still another object of the invention is to provide a thermometer and backing support therefor in which the thermometer and support may be separated simply when desired.

DESCRIPTION OF THE DRAWINGS

These and other objects and advantages of the invention will be understood more fully from the following detailed description thereof with reference to the accompanying drawings wherein.

DESCRIPTION OF THE PREFERRED EMBODIMENT

Figure 1:
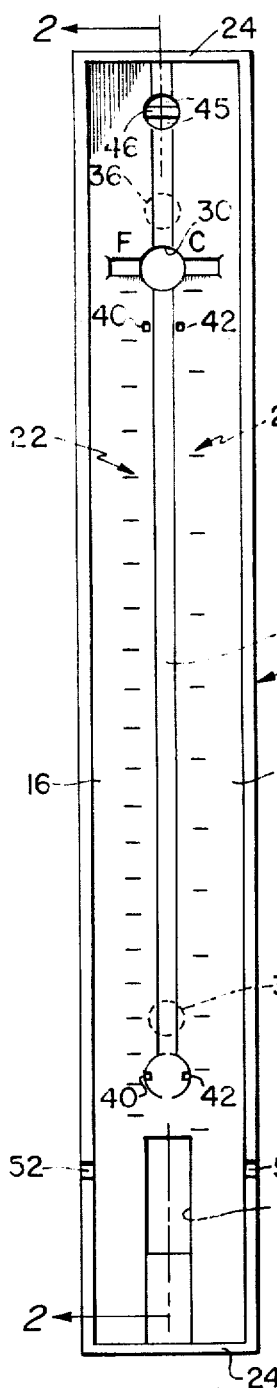
FIG. 1 is a front elevation of the thermometer backing member without the thermometer.

As shown in the drawings, the invention includes a conventional thermometer tube 10 having a bulb reservoir 12 at its lower end. The tube 10 is retained within a channel-shaped backing, indicated generally by the reference character 14 as shown in FIG. 1. The backing 14 is longer than the thermometer tube 10 and includes a pair of forwardly divergent sidewalls 16 which meet along the elongate apex 18. The entire backing 14 may be formed from a single piece of material such as polypropylene according to well-known plastic molding techniques. The backing should be able to withstand temperatures of between −10° C and 135°C as might be found in usual laboratory experiments.

The inner surface of each of the sidewalls 16 is provided with calibrated temperature scales 20, 22 which are disposed on either side of and embrace the thermometer tube 10. The scales 20, 22 preferably are molded directly into the sidewalls 16 when the backing 14 is formed but may also be provided by labels or other marking techniques. The backing 16 preferably includes end walls 24 which are formed integrally with the ends of the sidewalls 16 and apex 18 to rigidify further the backing.

Figure 3:
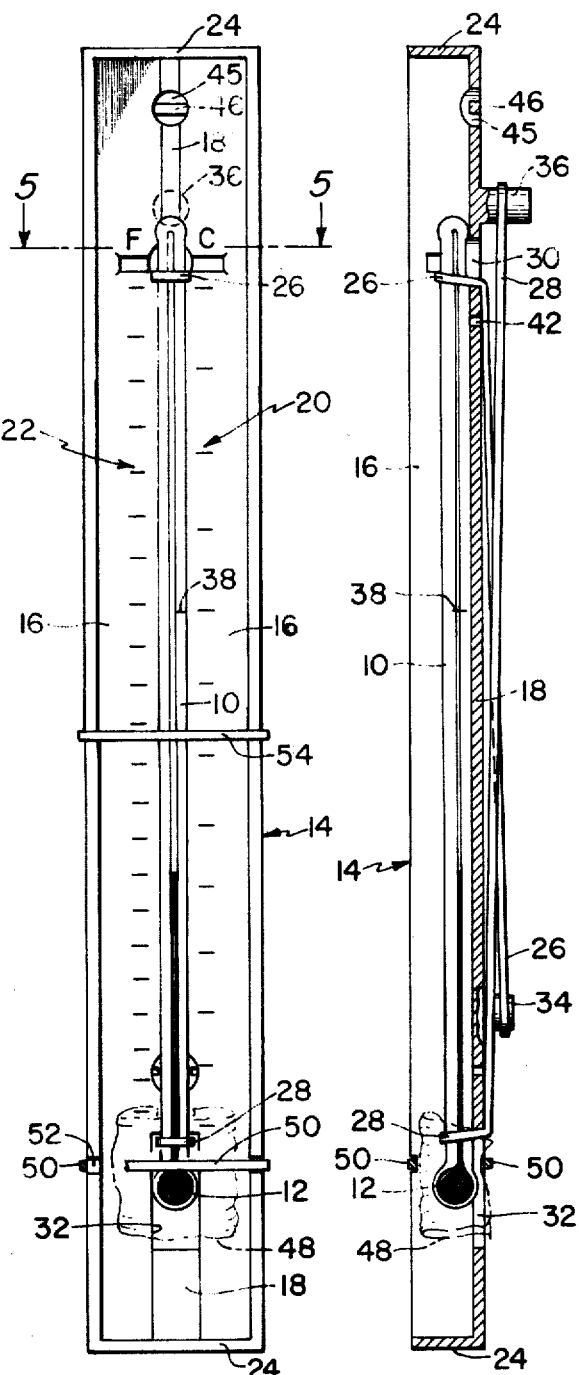
FIG. 3 is a front elevation of the device with the thermometer attached to the backing by elastic bands.
Figure 4:
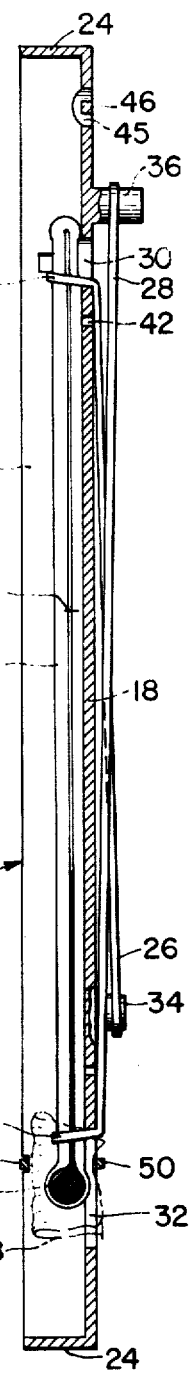
FIG. 4 is a side elevation, in section, of the arrangement shown in FIG. 3 as seen along the line 4—4 of FIG. 3.
Figure 5:
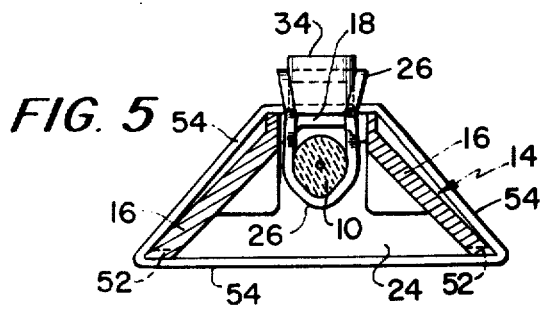
FIG. 5 is a section taken through the assembled thermometer and backing as seen along the line 5—5 of FIG. 3.

In the preferred embodiment of the invention, the thermometer is retained in place within the channel by a pair of elastic rubber bands 26, 28 which are looped about the upper and lower ends respectively of the thermometer tube 10 as shown in FIGS. 3, 4, and 5. The rubber bands 26, 28 extend rearwardly through upper and lower holes 30, 32 formed respectively near the upper and lower ends of the thermometer tube 10 in the apex 18 of the backing 14. The rear, free end of the upper rubber band 28 is stretched downwardly along the rear surface of the apex 18 and is looped about a rearwardly extending post 34 which is formed integrally with the backing 14. The free end of the lower elastic band 28 extends through the hole 32 and then upwardly along the rear surface of the apex 18 where it is looped about an upper rearwardly extending post 36 formed integrally with the backing 14 above the hole 30. This arrangement is effective to retain the thermometer tube 10 firmly within and along the apex 18 of the backing and also permits the thermometer tube 10 to be separated from the backing simply and quickly when desired. The elastics 26, 28 serve further to retain the thermometer tube 10 in place and prevent axial shifting of the tube 10 along the backing 14. This advantage is obtained when employing elastic bands fabricated from natural rubber or other high-friction material which will grip the glass tube 10 firmly. Furthermore, the resilient, flexible characteristics of the elastic band serve to reduce any shock or vibration which might be transmitted to the thermometer tube 10, for example, if the device is dropped inadvertently.

When assembling the thermometer tube 10 and backing 14, the tube is oriented properly along the apex 18 in relation to the temperature scales 20, 22 by a scratch mark 38 formed on the thermometer tube 10. The location of the scratch mark 38 along the thermometer tube is calibrated during its manufacture so that the scratch mark 38 will correspond to a particular temperature on the scales 20, 22. For example, in the illustrative embodiment of the invention, the thermometer tube 10 has been calibrated so that when assembling the tube and backing 14, the tube 10 is properly disposed along the apex 18 when the scratch mark 38 is in registry with the 70°C reading on the scale 22.

The feature of the invention which permits the tube 10 to be separated from the backing 14 simply is advantageous when the thermometer tube 10 is to be inserted through a relatively small opening, as in a stopper, which cannot receive the full cross-sectional area of the backing 14 itself. While the tube 10 is being used in its removed condition, the desired temperature reading may be taken by marking the thermometer tube with a grease pencil and then aligning the tube 10 so that the scratch mark 38 is properly disposed along the temperature scales 20, 22. The temperature reading of the alcohol or mercury column in the tube 10 may be read directly from the scales 20, 22.

Figure 2:
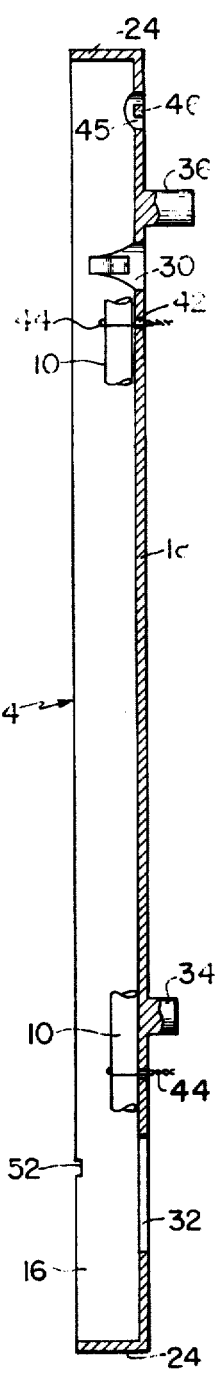
FIG. 2 is a side elevation, in section, of the backing as seen along the lines 2—2 of FIG. 1 and illustrating an alternative technique for securing the thermometer tube to the backing.

In some instances, it may be desirable to fasten the thermometer tube 10 more permanently to the backing 14. For this purpose, a pair of smaller, supplementary holes 40, 42 may be formed through the apex 18 near both of the upper and lower ends of the thermometer tube 10, preferably between the holes 30, 32 as shown in FIGS. 1 and 2. A thin wire 44 may be passed about the upper and lower end of the thermometer tube 10 and then through the holes 40, 42. The free ends of the wire may be twisted at the rear side of the backing 14 to secure the tube 10 firmly within the apex 13.

In the preferred embodiment of the invention, the upper end of the backing 14 includes a support hole 45 which may be formed in the apex 18 and preferably has a bar 46 extending across the hole to separate the hole into a pair of D-shaped portions. A string or wire may be looped about the bar 46 to hang the backing 14 or, as described below, to employ the device as a sling psychrometer.

The construction of the backing 14 and the recessed location of the thermometer tube well within the apex 18 permits the device to be employed as sling psychrometer. As shown in phantom in FIGS. 3 and 4, when employed in this mode, the bulb 12 is wrapped in a wet or wettable tissue 48 which is packed into the trough defined by the sidewalls. Additionally, the hole 32 is enlarged to permit a portion of the tissue 48 to be drawn rearwardly through the apex 18 near the bulb so that the bulb 12 may be wrapped fully about its outer surfaces by the tissue. The tissue 48 may be retained in place about the bulb and within the trough by an elastic band 50 which is wrapped about the backing 14 and the tissue 48. Slots 52 preferably are formed at the divergent edges of the sidewalls 16 near the region of the bulb to receive the elastic band 50 and help to retain it in place. This arrangement insures that as the entire device is swung about, all of the elements will remain in place.

A further aspect of the invention is that when taking a number of temperature readings, a particular reading or temperature may be employed as a reference by wrapping an elastic band about the backing as suggested at 54 in FIGS. 3 and 5. The elastic band 54 may be moved to any desired temperature setting along the length of the backing and the thermometer tube.

A further, not unimportant aspect, of the invention is that because of the configuration of the trough, the thermometer tube 10 is extremely well protected and is not likely to be damaged by inadvertent rough handling. The thermometer tube is retained well within the concave apex 18 of the backing and the sidewalls 16 and end walls 24 effectively isolate the fragile thermometer tube 10.

It should be understood that the foregoing description is intended merely to be illustrative of the invention and that other embodiments and modifications will be apparent to those skilled in the art without departing from its spirit.

Having thus described the invention, what is claimed is:

1. A temperature responsive measuring device preferably for use by students and having an elongated thermometer tube that is readily replaceable, said device comprising:
    an elongated backing having a front surface of concave configuration along its length, said front surface being defined by a pair of sidewalls diverging from an apex;
    a temperature scale disposed on said forward surface of at least one of said sidewalls;
    and means for mounting the thermometer tube within and along the concave apex of said backing, said sidewalls extending forwardly of and substantially beyond said thermometer tube to protect said tube;
    said means for mounting said thermometer tube comprising;
        a first hole formed in the upper portion of said backing,
        a second hole formed in the lower portion of said backing,
        first and second posts extending rearwardly from and spaced along the rear surface of said backing and each disposed adjacent but spaced from respective first and second holes,
        and at least one continuous and endless elastic band having a first segment extending through the first hole and being looped about the upper end of said thermometer tube, and a second segment that is stretched downwardly to extend and wrap about said rearwardly extending second post,
        whereby said thermometer tube may be readily replaced by removing the second segment from the post so as to loosen the first segment and permit easy withdrawal of the tube from the backing.

2. A temperature responsive measuring device as defined in claim 1 further comprising:
    said lower hole being formed so that when said thermometer tube which has a reservoir bulb is disposed in proper alignment with respect to said temperature scale, the reservoir bulb of said thermometer tube is disposed in alignment to said lower hole;

said lower hole being dismensioned so as to permit a moist tissue to be placed about said bulb; and means formed at the upper end of said backing for securing said upper end to a line thereby to enable said device to be employed as a psychrometer.

3. A temperature responsive measuring device as defined in claim 2 further comprising:

means for retaining said tissue about said bulb comprising a second elastic band wrapped about said backing and extending over said concave region to retain said tissue in said concave region.

4. A temperature responsive measuring device as defined in claim 3 further comprising:

means forming slots in the forward edge of each of said sidewalls near said lower hole to retain said second elastic band for holding said tissue in place.

5. A temperature responsive measuring device as defined in claim 4 wherein said second elastic band serves a dual function and is moveable along the length of said thermometer tube to enable said band to be registered at selected locations along the temperature scale.

6. A temperature responsive measuring device as defined in claim 1 wherein said backing is formed from polypropalene adapted to withstand a temperature range of between −10° and 135°C.

7. A temperature responsive measuring device as defined in claim 1 further comprising a second continuous and endless elastic band having a first segment extending through the lower hole and being looped about the lower end of the thermometer tube and a second segment extending about the first post.

8. For a temperature measuring device preferably for use by students and having an elongated thermometer tube that may on occasion have to be replaced and an elongated backing having a temperature scale disposed on the forward surface thereof, the improvement comprising means for mounting the thermometer along the backing and against the forward surface in a manner to permit easy replacement of the thermometer tube, said means for mounting comprising, means defining a top hole in an upper portion of said backing, said backing having a rear surface, a post spaced from the top hole and extending rearwardly from the rear surface of the backing, and a continuous and endless elastic band means that may be stretched and has opposite securing ends, one end extending through the top hole to form a loop which extends about the upper end of said thermometer tube, the other end being stretched downwardly away from the one end to form a loop that wraps about the rearwardly extending post, whereby said thermometer tube may be readily replaced by removing the looped other end of the elastic band means from the post so as to loosen the said one end of the elastic band means and permit easy withdrawal of the tube from the backing.

9. The improvement of claim 8 further comprising, means defining a lower hole in a lower portion of said backing and a top post spaced from both the first post and lower hole and extending rearwardly from the rear surface of the backing, said elastic band means also comprising, third and fourth loop end for extending and wrapping about the bottom end of the thermometer tube and the top post.

10. The improvement of claim 8 further comprising, means defining a lower hole in a lower portion of the backing, a top post spaced from both the first post and lower hole and extending rearwardly from the rear surface of the backing, and a second continuous and endless elastic band that may be stretched and has opposite securing ends, one end extending through the lower hole to form a loop which extends about the lower end of said thermometer tube, the other end being stretched upwardly away from the one end to form a loop that wraps about the rearwardly extending top post.

11. The improvement of claim 10 wherein said top post and top hole are spaced from each other and interconnected by a solid section of the backing, and the lower post and lower hole are spaced from each other and interconnected by a solid section of the backing.

12. The improvement of claim 11 wherein both elastic bands have two sections that extend through the holes to form loops.

* * * * *